(12) United States Patent
Bange et al.

(10) Patent No.: US 7,769,456 B2
(45) Date of Patent: Aug. 3, 2010

(54) FREQUENCY-AGILE SYSTEM FOR TELEMETRY WITH IMPLANTABLE DEVICE

(75) Inventors: Joseph E. Bange, Eagan, MN (US); Vineel Vallapureddy, Coon Rapids, MN (US); Kenneth F. Cowan, Kirkland, WA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1006 days.

(21) Appl. No.: 11/469,804

(22) Filed: Sep. 1, 2006

(65) Prior Publication Data

US 2008/0055070 A1 Mar. 6, 2008

(51) Int. Cl.
*A61N 1/372* (2006.01)
*A61N 1/37* (2006.01)

(52) U.S. Cl. .............. 607/30; 607/31; 607/32; 607/60; 340/539.12

(58) Field of Classification Search .......... 607/30–32, 607/60
See application file for complete search history.

(56) References Cited

U.S. PATENT DOCUMENTS

| | | | |
|---|---|---|---|
| 5,287,384 A | 2/1994 | Avery et al. | |
| 5,342,408 A | 8/1994 | deCoriolis et al. | |
| 5,562,713 A | 10/1996 | Silvian | |
| 5,568,510 A | 10/1996 | Tam | |
| 5,729,680 A * | 3/1998 | Belanger et al. ............ 709/222 |
| 5,940,384 A | 8/1999 | Carney et al. | |
| 6,535,766 B1 | 3/2003 | Thompson et al. | |
| 6,763,269 B2 | 7/2004 | Cox | |
| 6,801,807 B2 | 10/2004 | Abrahamson | |
| 6,868,288 B2 | 3/2005 | Thompson | |
| 7,013,178 B2 | 3/2006 | Reinke et al. | |
| 7,218,969 B2 | 5/2007 | Vallapureddy et al. | |
| 2003/0149459 A1 | 8/2003 | Von Arx et al. | |
| 2003/0220673 A1* | 11/2003 | Snell ...................... 607/60 |
| 2006/0030903 A1 | 2/2006 | Seeberger et al. | |
| 2006/0161223 A1 | 7/2006 | Vallapureddy et al. | |
| 2007/0185550 A1 | 8/2007 | Vallapureddy et al. | |

FOREIGN PATENT DOCUMENTS

| | | |
|---|---|---|
| EP | 1308184 A2 | 5/2003 |
| EP | 1495783 A1 | 1/2005 |
| WO | WO-99/12302 A1 | 3/1999 |
| WO | WO-2006020546 A1 | 2/2006 |

OTHER PUBLICATIONS

Bange, Joseph E., et al., "Implantable Medical Device Telemetry With Adaptive Frequency Hopping", U.S. Appl. No. 11/456,937, filed Jul. 12, 2006, 35 pages.

(Continued)

*Primary Examiner*—Carl H Layno
*Assistant Examiner*—Natasha N Patel
(74) *Attorney, Agent, or Firm*—Schwegman, Lundberg & Woessner, P.A.

(57) ABSTRACT

The present disclosure relates to an RF telemetry system and method for enabling communication between an implantable medical device and an external device with an improved tolerance to noise from external sources. Multiple communications channels at different frequencies are provided which are synchronously switched between during a communications session by both devices.

20 Claims, 7 Drawing Sheets

OTHER PUBLICATIONS

Bange, Joseph E., et al., "Implantable Medical Device Telemetry With Periodic Frequency Hopping", U.S. Appl. No. 11/456,942, filed Jul. 12, 2006, 43 Pages.

U.S. Appl. No. 11/039,200, Non Final Office Action mailed Aug. 3, 2006, 10 pgs.

U.S. Appl. No. 11/039,200, Notice of allowance mailed Dec. 15, 2006, 4 pgs.

U.S. Appl. No. 11/039,200, Response filed Nov. 2, 2006 to Non Final Office Action mailed Aug. 3, 2006, 9 pgs.

PCT Application No. PCT/US2007/072827, International Search Report mailed Dec. 10, 2007, 4 pgs.

PCT Application No. PCT/US2007/072827, Written Opinion mailed Dec. 10, 2007, 6 pgs.

* cited by examiner

Fig. 1

| Time Period | Channel |
|---|---|
| T0 | C0 |
| T1 | C9 |
| T2 | C13 |
| T3 | C4 |
| T4 | C15 |
| T5 | C6 |
| T6 | C1 |
| T7 | C11 |
| T8 | C5 |
| T9 | C14 |
| T10 | C7 |
| T11 | C2 |
| T12 | C12 |
| T13 | C8 |
| T14 | C3 |
| T15 | C10 |

| Time Period | Channel |
| --- | --- |
| T0 | C16 |
| T1 | C9 |
| T2 | C13 |
| T3 | C4 |
| T4 | C15 |
| T5 | C6 |
| T6 | C18 |
| T7 | C11 |
| T8 | C5 |
| T9 | C14 |
| T10 | C7 |
| T11 | C17 |
| T12 | C12 |
| T13 | C8 |
| T14 | C19 |
| T15 | C10 |

| Time Period | Channel |
|---|---|
| T0 | C9 |
| T1 | C13 |
| T2 | C4 |
| T3 | C15 |
| T4 | C6 |
| T5 | C11 |
| T6 | C5 |
| T7 | C14 |
| T8 | C7 |
| T9 | C12 |
| T10 | C8 |
| T11 | C10 |

| Time Period | Channel |
|---|---|
| T0 | C9 |
| T1 | C13 |
| T2 | C4 |
| T3 | C15 |
| T4 | C6 |
| T5 | C11 |
| T6 | C5 |
| T7 | C14 |
| T8 | C7 |
| T9 | C12 |
| T10 | C8 |
| T11 | C10 |
| T12 | C19 |
| T13 | C16 |
| T14 | C18 |
| T15 | C17 |

Fig. 10

| Channel Index | Channel | Bitmask | Resulting Synchronous Scan List |
|---|---|---|---|
| 0 | C0 | 0 | Skip |
| 1 | C9 | 1 | C9 |
| 2 | C13 | 1 | C13 |
| 3 | C4 | 1 | C4 |
| 4 | C15 | 1 | C15 |
| 5 | C6 | 1 | C6 |
| 6 | C1 | 0 | Skip |
| 7 | C11 | 1 | C11 |
| 8 | C5 | 1 | C5 |
| 9 | C14 | 1 | C14 |
| 10 | C7 | 1 | C7 |
| 11 | C2 | 0 | Skip |
| 12 | C12 | 1 | C12 |
| 13 | C8 | 1 | C8 |
| 14 | C3 | 0 | Skip |
| 15 | C10 | 1 | C10 |
| 16 | C19 | 1 | C19 |
| 17 | C16 | 1 | C16 |
| 18 | C18 | 1 | C18 |
| 19 | C17 | 1 | C17 |

Fig. 11

FREQUENCY-AGILE SYSTEM FOR TELEMETRY WITH IMPLANTABLE DEVICE

RELATED APPLICATIONS

This application is related to U.S. patent application Ser. No. 11/039,200, filed on Jan. 19, 2005, now issued as U.S. Pat. No. 7,218,969, the disclosure of which is hereby incorporated by reference.

FIELD OF THE INVENTION

This invention pertains to implantable medical devices such as cardiac pacemakers and implantable cardioverter/defibrillators. In particular, the invention relates to a system and method for implementing telemetry in such devices.

BACKGROUND

Implantable medical devices (IMDs), including cardiac rhythm management devices such as pacemakers and implantable cardioverter/defibrillators, typically have the capability to communicate data with an external device (ED) via a radio-frequency telemetry link. One such external device is an external programmer used to program the operating parameters of an implanted medical device. For example, the pacing mode and other operating characteristics of a pacemaker are typically modified after implantation in this manner. Modern implantable devices also include the capability for bidirectional communication so that information can be transmitted to the programmer from the implanted device. Among the data that may typically be telemetered from an implantable device are various operating parameters and physiological data, the latter either collected in real-time or stored from previous monitoring operations.

External programmers are commonly configured to communicate with an IMD over an inductive link. Coil antennas in the external programmer and the IMD are inductively coupled so that data can be transmitted by modulating a carrier waveform which corresponds to the resonant frequency of the two coupled coils. An inductive link is a short-range communications channel requiring that the coil antenna of the external device be in close proximity to the IMD, typically within a few inches. Other types of telemetry systems may utilize far-field radio-frequency (RF) electromagnetic radiation to enable communications between an IMD and an ED over a wireless medium. Such long-range RF telemetry allows the IMD to communicate with an ED, such as an external programmer or remote monitor, without the need for close proximity. In either the home or the clinic, however, there are external sources of RF energy which may interfere with communication between the ED and IMD.

SUMMARY

The present disclosure relates to an RF telemetry system and method for enabling communication between an implantable medical device and an external device with an improved tolerance to noise from external sources. Multiple communications channels at different frequencies are provided which are synchronously switched between during a communications session by both devices.

DETAILED DESCRIPTION

Described below is a system and method for providing wireless RF telemetry between an implantable medical device and an external device with improved tolerance to external noise. Most noise from external sources is of the narrow-band type, where the energy of the noise is confined to a particular frequency range. Examples of narrow-band noise sources include communications devices such as wireless telephones as well as many other kinds of electronic equipment which are commonly found in the home and in the clinic. When such narrow-band noise is in the same frequency range used for telemetry, it is said to be in-band and can interfere with communications between the devices.

In order to deal with the problem of in-band noise, the available bandwidth of the wireless medium is divided into multiple communications channels at different frequencies. At any given time, only the channels at the same frequency as the in-band noise are interfered with. In the system and method described herein, the external device and implantable device are programmed with a frequency-hopping scheme such that the devices synchronously switch from channel to channel at predetermined times according to a synchronous channel scan list during a communications session in order to minimize the effects of noise in one of the channels. The synchronous channel scan list defines a plurality of time slots making up a frequency-hopping frame and specifies which channel is to be used for each time slot. If a frequency-hopping failure occurs at a particular channel, as determined by detecting some specified amount of performance degradation in that channel, the failed channel may be removed from the synchronous channel scan list. The time slot for the failed channel may then be removed from the synchronous channel list which makes the frequency-hopping frame shorter. Alternatively, the synchronous channel list may be modified to specify a previously unused channel for the time slot previously assigned to the failed channel. The system may combine both methods for modifying the synchronous channel scan list. For example, the system may try to keep the number of time slots in the frequency-hopping frame constant by substituting a previously unused channel for a failed channel in the synchronous channel scan list if such an unused channel is available and deleting the time slot for the failed channel otherwise.

In order to detect a frequency-hopping failure, one or both of the external and implantable devices may be configured to monitor channel quality. Channel quality may be monitored, for example, by monitoring particular quality parameter, such as the data transfer rate or throughput, during a communications session and comparing it to a threshold value. Alternative quality parameters such as the error rate, the number of repeated frames during a communications session, or the length of time in which no data transfer has taken place could also be compared to threshold values.

1. Exemplary Hardware Platform

Figure 1:
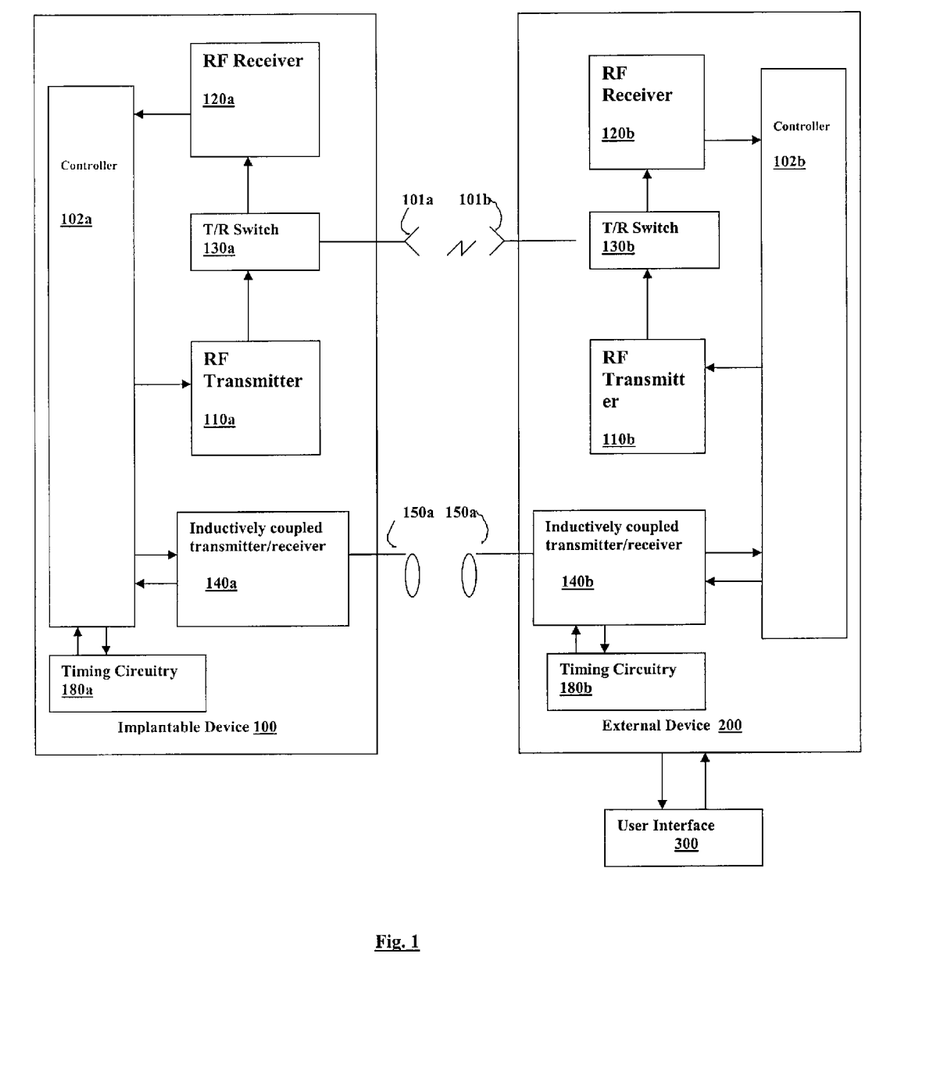
FIG. 1 is a block diagram of a telemetry system for an implantable device and an external device.

FIG. 1 shows the primary telemetry components of an external device 200 and an implantable medical device 100. In this functional block diagram, the components are shown as being identical in each device. In this exemplary embodiment, the external device and the implantable device are microprocessor-based devices each having a controller 102a or 102b that supervises overall device operation as well as telemetry. The controllers in each device may be implemented as microprocessor-based controllers and include a microprocessor and memory for data and program storage, implemented with dedicated hardware components such as ASICs (e.g., as a finite state machine), or implemented as a combination thereof. As the term is used herein, the programming of the controller refers to either code executed by a microprocessor or to specific configurations of the hardware components. The implantable device 100 may be a cardiac rhythm management device such as a pacemaker or implantable cardioverter/defibrillator, while the external device 200 may be an external programmer or a data-gathering device such as remote monitor. A user interface 300 (e.g., a keyboard and monitor) may be provided to enable a user such as a clinician to direct the operation of the external device.

A long-range RF receiver 120a or 120b and a long-range RF transmitter 110a or 110b are interfaced to the controller 102a or 102b in the implantable device and the external device, respectively. Also in each device, the transmitter and receiver are coupled to an antenna 101a or 101b through a transmit/receive switch 130a or 130b. The transmit/receive switches 130a and 130b are controlled by the microprocessor and either passes radio-frequency signals from the transmitter to the antenna or from the antenna to the receiver to establish an RF link. To effect communications between the devices over the RF link, a radio-frequency carrier signal modulated with digital data is transmitted wirelessly from one antenna to the other. A demodulator for extracting digital data from the carrier signal is incorporated into each receiver, and a modulator for modulating the carrier signal with digital data is incorporated into each transmitter. The interface to the controller for the RF transmitter and receiver in each device enables data transfer. The RF receiver and transmitter of each device are tunable and may be switched among a plurality of communications channels which differ in frequency. The implantable device also incorporates a means by which the controller can power up or power down the RF receiver and/or transmitter in order to manage duty cycles and conserve battery energy. External clocking circuitry 180a and 180b are also shown for the external and implantable devices that supply clock signals for controller operation and for implementing timers in either code executed by the controller or by discrete components. Synchronized timers of each device are used to implement frequency hopping frames and the time slots contained therein. During operation, clock synchronizing signals may be transmitted between the devices to maintain synchronous channel switching in accordance with the synchronous channel scan list. FIG. 1 also shows an inductively coupled transmitter/receiver 140a or 140b and antenna 150a or 150b for the implantable and external devices by which communication may take place over an inductive link when the two devices are in close physical proximity to one another.

2. Exemplary Frequency-Hopping Scheme

In the embodiments described below, the controllers of the external and implantable devices are programmed to operate their respective telemetry hardware in a manner which utilizes multiple communications channels. The multiple channels are defined with different carrier frequencies so that communications over one channel does not disturb communications over any of the other channels.

An exemplary telemetry system for enabling radio-frequency (RF) communications between an implantable medical device and an external device over a wireless medium includes an antenna, an RF transmitter, an RF receiver, and a controller incorporated into each of the implantable and external devices, where the RF transmitter and receiver of each device are tunable and may be switched among a plurality of different communications channels which differ in frequency. The controller is interfaced to the RF transmitter and receiver in each device to enable data transfer over a selected channel. The external device and implantable device controllers are programmed to synchronously switch among a plurality of communications channels during a communications session according to a synchronous channel scan list that specifies which communications channel is to be used at a particular time. The controllers of the implantable and external devices are programmed to use associated timing circuitry to divide time into frequency hopping frames each of which contains a plurality of time slots of defined length. The synchronous channel scan list then specifies the number of time slots within each frequency hopping frame and assigns a communications channel that is to be used for data transfer during each time slot.

The synchronous channel scan list may be initially specified by programming the external device via its user interface. The external device then transmits the synchronous channel scan list to the implantable device. The implantable and external device controllers may also be programmed such that the synchronous channel list may be modified during a communications session in order to add or remove communications channels and/or time slots. For example, upon detection of a frequency-hopping failure for a particular channel by one of the devices, as determined by detecting degradation in performance for that channel, the failure is communicated to the other device during the communications session. A modified synchronous channel scan list may then be also communicated between the devices which deletes the failed channel from the list and discontinues its further use. In another example, a channel previously unavailable for use may become available, and a modified synchronous channel scan list may then be communicated between the devices that adds the channel to the list. Use of the synchronous channel list may also be suspended if conditions warrant. For example, the external device may determine that a particular channel is free from interference and decide that further communications should proceed only on that channel by transmitting a command to the implantable device that suspends further frequency hopping. Frequency hopping may then be restarted if communications on the channel should subsequently become degraded.

As described above, the implantable and external device controllers may be programmed such that the synchronous channel scan list may be modified to remove one or more particular communications channels from the synchronous channel scan list upon detection of degradation in the quality of those particular communications channels. Such modification of the synchronous channel scan list may be restricted to one device or may be capable of being performed by both devices. For example, the external device controller may be programmed to modify the synchronous channel scan list by removing one or more particular communications channels from the list upon detection of degradation in the quality of those particular communications channels and to transmit the modified synchronous channel scan list to the implantable device.

In one embodiment, the controllers of each device are programmed such that when a particular communications channel is removed from the synchronous channel scan list, the time slot assigned to the removed communications channel is assigned to another communications channel. The time slot for the failed channel would preferably be assigned to a previously unused channel, but the time slot could also be assigned to a channel already in use so that a channel is used for more than one time slot. In another embodiment, the controllers are programmed such that when a particular communications channel is removed from the synchronous channel scan list, the time slot assigned to the removed communications channel is deleted from the frequency hopping frame. The frequency-hopping frame then becomes shorter by containing fewer time slots. The two embodiments may be combined by programming the controllers such that when a particular communications channel is removed from the synchronous channel scan list, the time slot assigned to the removed communications channel is assigned to another previously unused communications channel or, if no previously unused communications channel is available, the time slot assigned to the removed communications channel is deleted from the frequency hopping frame.

In one embodiment, the synchronous channel scan list is a subset of a master channel scan list whose entries may be enabled or disabled to form the synchronous channel scan list. The external device may then modify the synchronous channel scan list to remove a particular communications channel from the synchronous channel scan list upon detection of degradation in the quality of that communications channel by transmitting a command to the implantable device that disables the entry for that communications channel in the master channel scan list. Similarly, the external device may modify the synchronous channel scan list to add a particular communications channel to the synchronous channel scan list by transmitting a command to the implantable device that enables the entry for that communications channel in the master channel scan list. Such enablement and disablement commands may be implemented, for example, by a channel scan mask that enables or disables entries of the master channel scan list.

FIGS. 2 through 11 illustrate example embodiments of the frequency hopping scheme described above in which an external programmer recorder monitor (PRM) and an implanted pulse generator (PG) device use frequency hopping over a set of M-ary RF frequencies. The channel sets that the PRM and PG hop over are changeable while maintaining communications. In this scheme, the PRM and PG have a set of channels in a specified order in which to hop as defined by a synchronous channel scan list. Two methods that allow the set of channels to be modified while maintaining communications are illustrated. The first method is channel reassignment to an alternate frequency, while the second method is channel removal. The two methods can be used independently or combined into a hybrid approach.

Figure 2:
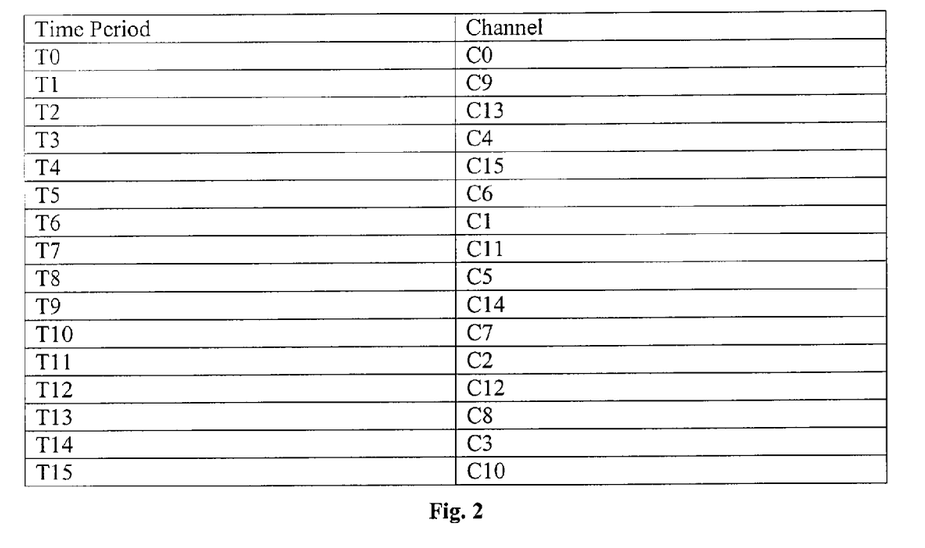
FIGS. 2 through 11 illustrate example embodiments of the frequency hopping scheme as described herein.
Figure 3:
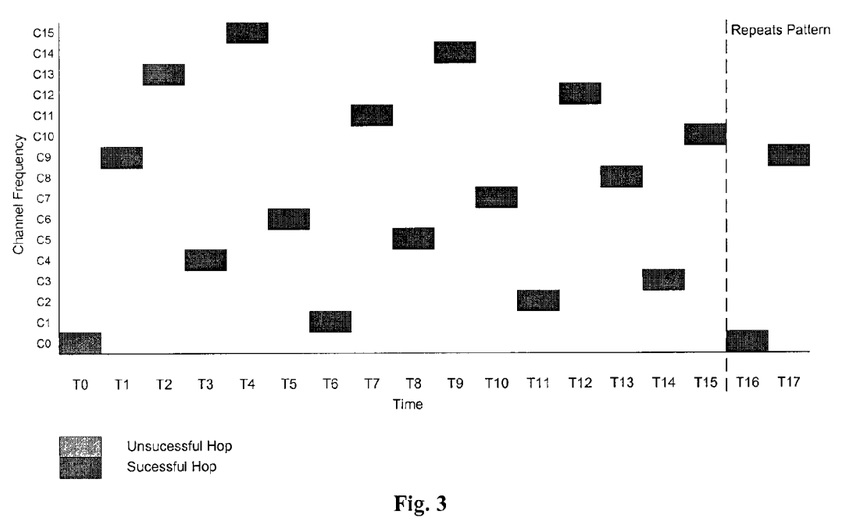

FIG. 2 shows an example of a synchronous channel scan list that implements frequency hopping over a set of 16 channels by assigning each of the time slots T0 through T15 making up a frequency hopping frame to one of channels C0 through C15. FIG. 3 illustrates the frequency hopping. As a time interval for a particular time slot expires, the PRM and PG simultaneously change channels to the next channel in the list. For example, when the time slot T1 expires, the frequency is changed from channel 9 to channel 13, and when T2 expires the frequency changes to channel 4. When the end of the scan list is reached the system hops back to the beginning of the list and continues as another frequency hopping frame. In this example, when T15 expires the channel changes from C10 to C0 which is assigned to the T0 interval.

Figure 4:
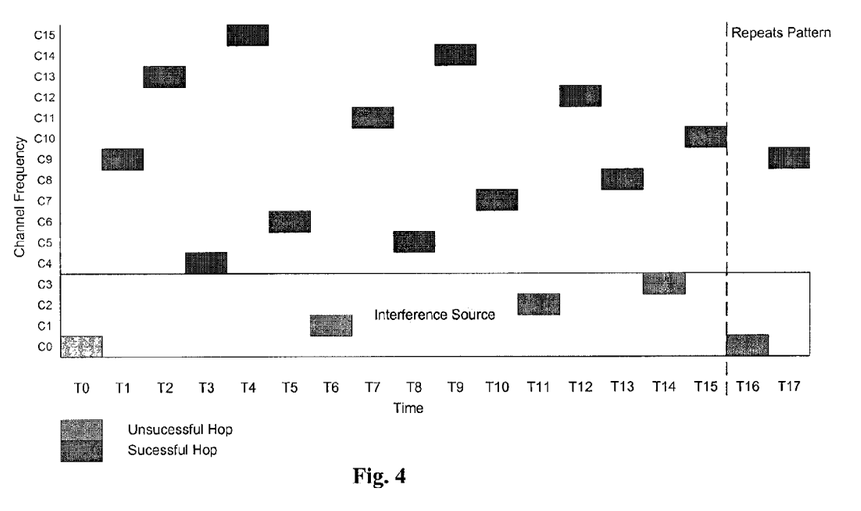
Figure 5:
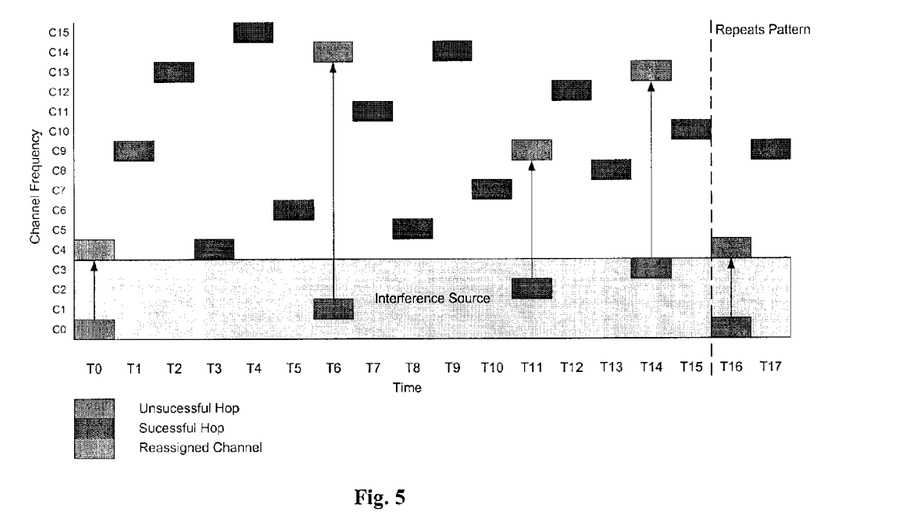
Figure 6:
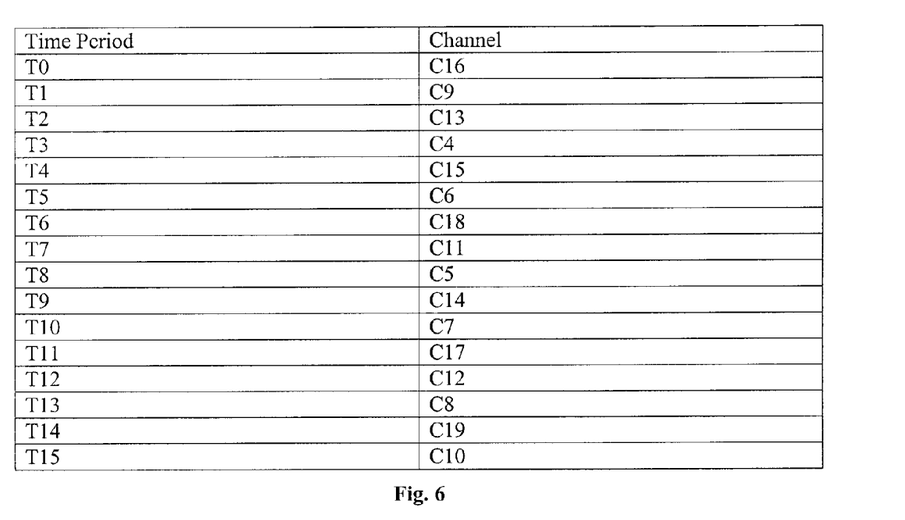

FIG. 4 illustrates the same frequency hopping as in FIG. 3 where a static interferer causes frequency hopping failures in channels C0-C3. One method to adapt to the interference source is to reassign the channels that do not work due to the interference to other channels. FIG. 5 shows how the time slots previously assigned to channels C0-C3 may be reassigned to channels C16-C19, and FIG. 6 shows the corresponding modified synchronous channel scan list. The number of channels in the repeat pattern has not changed, but the channels assigned to the time slots have. The newly assigned channels could be channels that are already used in another time slot or the channel could be a previously unused channel. For this example the channels are previously unused channels.

Figure 7:
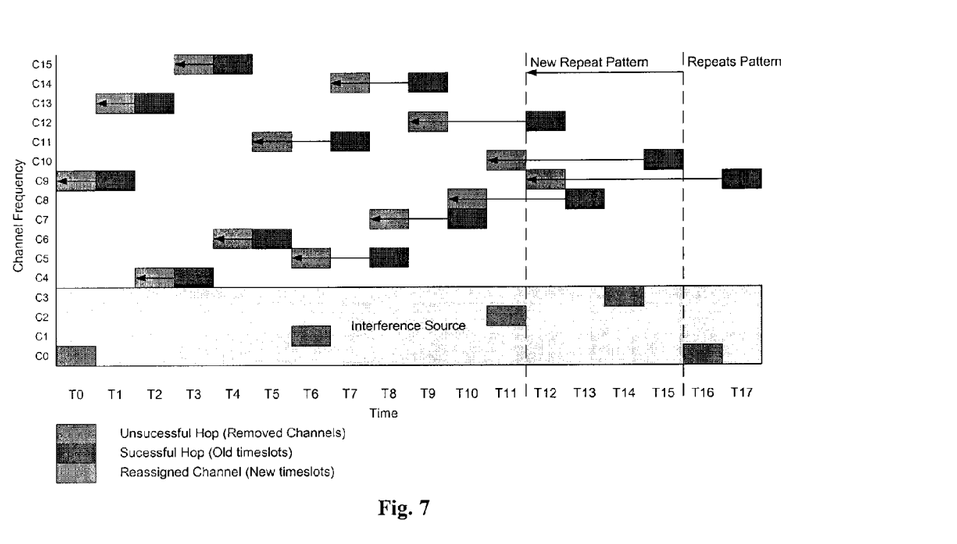
Figure 8:
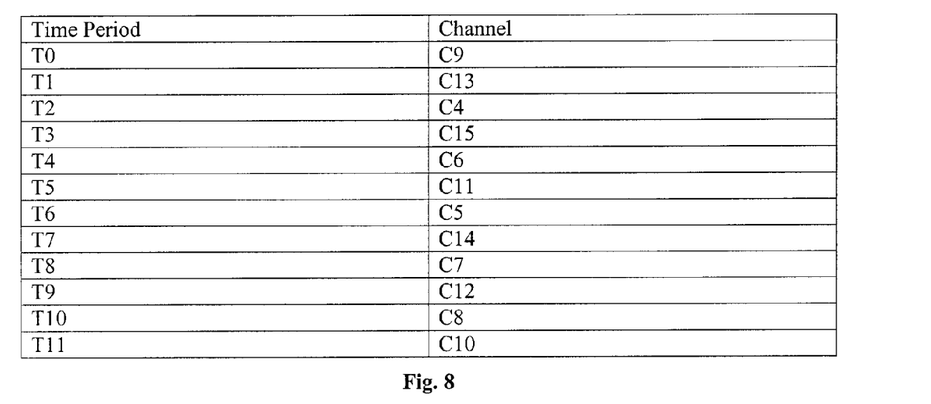

Another method to adapt the channel hopping sequence is to remove channels from the synchronous channel scan list. The result of removing channels C0-C3 would result in a hoping sequence as shown in FIG. 7 and a modified synchronous channel scan list as shown in FIG. 8. Note that the channel hopping list has been shortened from 16 channels to 12 channels in this example by removing the four poor performing channels. The arrows in FIG. 7 show how, as channels are removed from the channel hopping list, the remaining channels slide to the left into earlier time slots.

As used herein, the term channel has been used to refer to a particular RF frequency over which communications may take place. A channel may be referred to in terms of its physical attributes such as center frequency and bandwidth, termed a physical channel. The PRM and PG hardware need to be provided with the programming information associated with each physical channel that might be tuned to during a communication session. The programming information for each of the physical channels may be stored into an array known as the physical channel list. The physical channel attributes can then be referenced using an index into the physical channel list, known as the logical channel.

Figure 9:
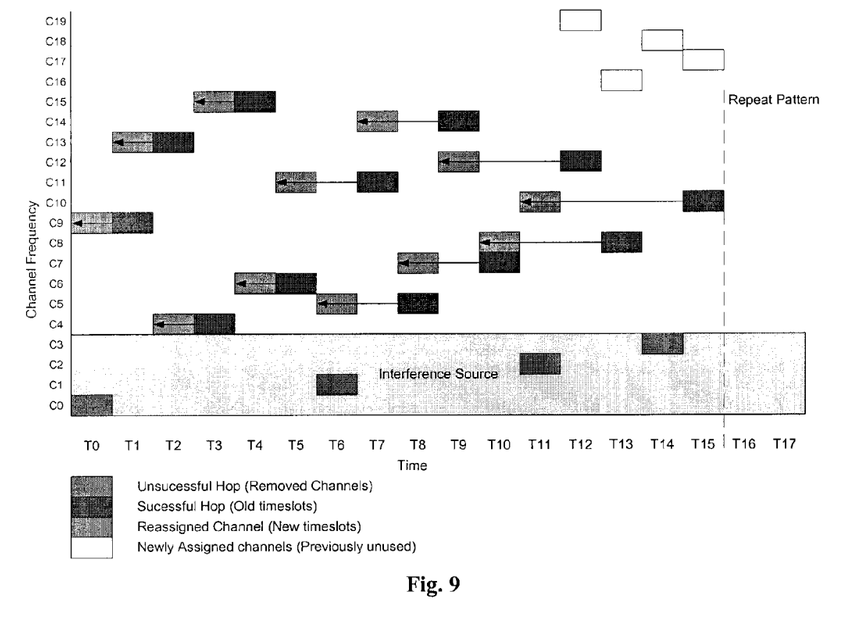
Figure 10:
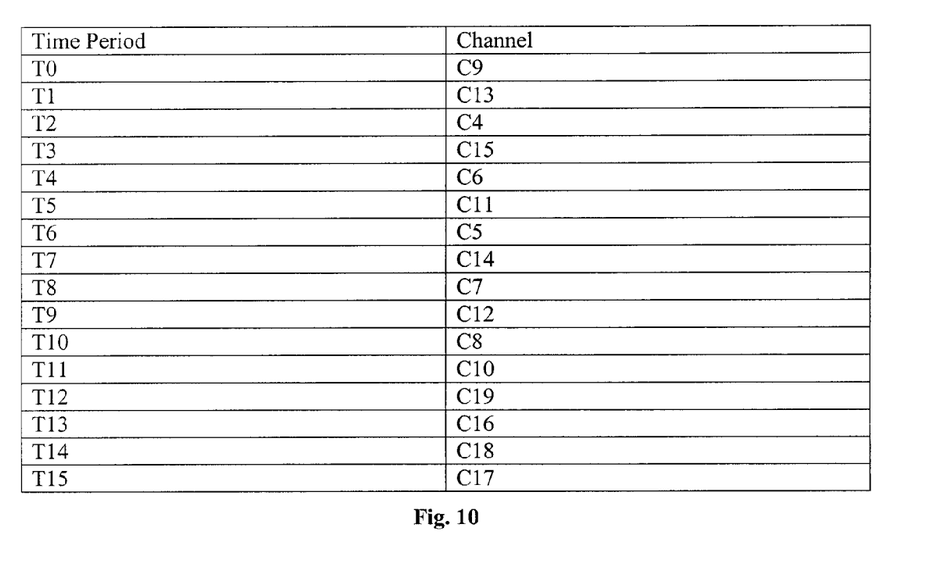
Figure 11:
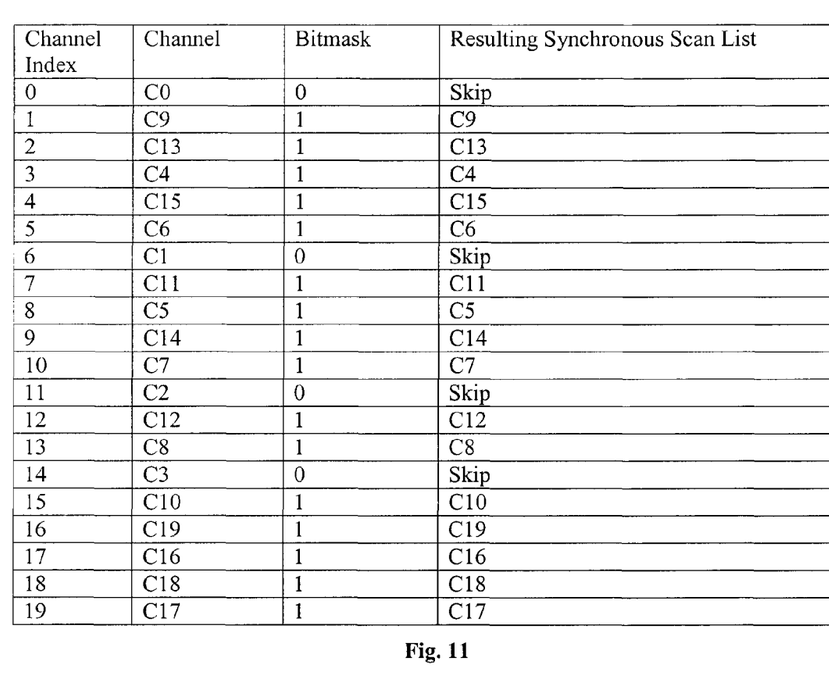

In one embodiment, the synchronous channel scan list may hold an array of logical channels in an order that determines the order in which frequency hopping occurs. That is, the particular time slot to which each channel is assigned is determined by the order in which the channels appear in the synchronous channel scan list. A master channel scan list may be generated that lists all available channels in a particular order. The synchronous channel scan list used for frequency hopping may then be defined as a subset of the master channel scan list, where the synchronous channel scan list is generated using a channel bit mask that enable/disable specific channels of the master channel scan list. In one example, the master channel scan list is 64 entries long and indexed with the numbers 0 to 63. The synchronous channel mask is then 64 bits in size with the LSB (D0) being mapped to master channel scan list index 0 and the MSB (D63) being mapped to master channel scan list index 63. The actual number of channels in the list is set by the available bandwidth for use divided by the bandwidth required for a single channel. To modify the synchronous channel scan list to change frequencies for poor performing channels, the PRM issues a SetScanChannelList command to the PG that contains the new channel and frequency assignments. Variations of the SetScanChannelList allow for modifications to replace the entire master channel scan list or a subset of the master channel scan list. Returning to the example for the channel reassignment method described above with reference to FIGS. 5 and 6, a single command could be used to reassign all 16 channels (only four of which are changed from the original list) or individual commands could be issued to reassign the poor performing channels (in this case four of them). When the PG acknowledges the receipt of the new channel(s) assignments, both the PRM and PG begin using the new master channel scan list. This method is best implemented by allowing the master channel scan list to be modified while the PRM and PG are communicating on channels that are working well and are not being reassigned. This prevents the loss of communication while the reassignment command is being processed. This command could be issued on lesser performing links but the performance would not be as good. To modify the list using the channel removal method a SetChannelBitmask command is issued from the PRM to the PG. This command modifies the bitmask that enables and disable channels in the master channel scan list and forms the synchronous channel scan list. Returning to the example in FIGS. 7 and 8, the bitmask in this case would be modified from the value 0x000000000000FFFF to 0x000000000000B7BE. An alternate way to use the SetChannelBitmask command would be to disable the four poor performing channels and enable four new channels. This method would require the master channel scan list to have additional entries that could be enabled. FIGS. 9 and 10 illustrate the resulting frequency hopping and the corresponding synchronous channel scan list using this method. FIG. 11 shows an example of a synchronous channel scan list generated using a particular master channel scan list and channel bitmask. In the last column the word 'Skip' is used to indicate that the channel is masked out and not included in the resulting synchronous master channel scan list.

Various techniques may be used in implementing the functions performed by the embodiments described above. Examples of such techniques are described in the following paragraphs.

Initiation of a communications session may involve a handshaking procedure in which control frames are transmitted to synchronize the subsequent activity of both devices. For example, when the external device wishes to transmit data, an RTS frame is transmitted to the implantable device which then responds with a CTS frame. Similarly, when the external device wishes to receive data, an RRTS frame is transmitted to the implantable device, the implantable device responds with an RTS frame, and the external device transmits a CTS frame. One or more of the control frames may also contain other information such as the device ID, amount of data to be transmitted, and an identification of which channel is to be used for data transfer. The device receiving a CTS frame then begins transmitting data frames. During the data transfer, data frames sent by one of the devices are acknowledged by the other device with an ACK frame and repeated if necessary in order to ensure reliable data transmission.

Once a communications session has been established and data transfer is taking place over a selected data channel, environmental noise or other factors may disrupt communications over the channel. Both the external and implantable devices may be programmed to monitor the data transfer in order to determine if the quality of the link has fallen below a specified level so as to constitute an interruption of the communications session and a frequency-hopping failure. For example, a frequency-hopping failure may be declared if the channel throughput falls below a certain level over a certain time (e.g., below 50% of channel capacity for 1 second), if a specified number of data frames are unacknowledged, and/or if the frame error rate exceeds a threshold value.

The implantable device may be equipped with a wake up timer for the telemetry components in order to conserve energy. Such an implantable device not engaged in an active communications session wakes up periodically from a low-power state and monitors transmissions on one or more designated channels to determine if an external device is attempting to communicate with it. After establishing communications, the external device transmits a clock synchronizing signal to the implantable device that enables the devices to use the synchronous channel scan list for further communications.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A telemetry system for enabling radio-frequency (RF) communications between an implantable medical device and an external device over a wireless medium, comprising:
   an antenna, an RF transmitter, an RF receiver, and a controller incorporated into each of the implantable and external devices, wherein the RF transmitter and receiver of each device are tunable and may be switched among a plurality of different communications channels which differ in frequency;
   wherein the controller is interfaced to the RF transmitter and receiver in each device to enable data transfer over a selected channel;
   wherein the controllers of the implantable and external devices are programmed to use associated timing circuitry to divide communications session time into frequency hopping frames each of which contains a plurality of session time slots of defined length; and,
   wherein the external device and implantable device controllers are programmed to synchronously switch, upon expiration of a predetermined session time slot, among a plurality of communications channels during a communications session according to a synchronous channel scan list that specifies the number of session time slots within each frequency hopping frame and assigns a communications channel that is to be used for data transfer during each session time slot while maintaining communications.

2. The system of claim 1 wherein the implantable and external device controllers are programmed such that the synchronous channel list may be modified during a communications session in order to add or remove communications channels and/or time slots.

3. The system of claim 2 wherein the implantable and external device controllers are programmed such that the synchronous channel scan list may be modified to remove one or more particular communications channels from the synchronous channel scan list upon detection of a degradation in the quality of those particular communications channels.

4. The system of claim 3 wherein the implantable and external device controllers are programmed such that when a particular communications channel is removed from the synchronous channel scan list, the time slot assigned to the removed communications channel is assigned to another communications channel.

5. The system of claim 3 wherein the implantable and external device controllers are programmed such that when a particular communications channel is removed from the synchronous channel scan list, the time slot assigned to the removed communications channel is deleted from the frequency hopping frame.

6. The system of claim 3 wherein the implantable and external device controllers are programmed such that when a particular communications channel is removed from the synchronous channel scan list, the time slot assigned to the removed communications channel is assigned to another previously unused communications channel or, if no previously unused communications channel is available, the time slot assigned to the removed communications channel is deleted from the frequency hopping frame.

7. The system of claim 3 wherein the external device controller is programmed to modify the synchronous channel scan list to remove one or more particular communications channels from the synchronous channel scan list upon detection of a degradation in the quality of those particular communications channels and to transmit the modified synchronous channel scan list to the implantable device.

8. The system of claim 2 wherein the synchronous channel scan list is a subset of a master channel scan list whose entries may be enabled or disabled to form the synchronous channel scan list.

9. The system of claim 8 wherein the implantable and external device controllers are programmed such that the external device may modify the synchronous channel scan list to remove a particular communications channel from the synchronous channel scan list upon detection of a degradation in the quality of that communications channel by transmitting a command to the implantable device that disables the entry for that communications channel in the master channel scan list and to add a particular communications channel to the synchronous channel scan list by transmitting a command to the implantable device that enables the entry for that communications channel in the master channel scan list.

10. The system of claim 8 wherein the implantable and external device controllers are programmed such that the external device may modify the synchronous channel scan list by transmitting to the implantable device a channel scan mask that enables or disables entries of the master channel scan list.

11. A method for enabling radio-frequency (RF) telemetry communications between an implantable medical device and an external device over a wireless medium, comprising:
- defining a plurality of different communications channels which differ in frequency;
- programming the implantable and external devices to use associated timing circuitry to divide communications session time into frequency hopping frames each of which contains a plurality of session time slots; and,
- programming the external device and implantable device to synchronously switch, upon expiration of a predetermined session time slot, among a plurality of communications channels during a communications session according to a synchronous channel scan list that specifies the number of time slots within each frequency hopping frame and assigns a communications channel that is to be used for data transfer during each session time slot while maintaining communications.

12. The method of claim 11 further comprising programming the implantable and external device controllers such that the synchronous channel list may be modified during a communications session in order to add or remove communications channels and/or time slots.

13. The method of claim 12 further comprising programming the implantable and external devices such that the synchronous channel scan list may be modified to remove one or more particular communications channels from the synchronous channel scan list upon detection of a degradation in the quality of those particular communications channels.

14. The method of claim 13 further comprising programming the implantable and external devices such that when a particular communications channel is removed from the synchronous channel scan list, the time slot assigned to the removed communications channel is assigned to another communications channel.

15. The method of claim 13 further comprising programming the implantable and external devices such that when a particular communications channel is removed from the synchronous channel scan list, the time slot assigned to the removed communications channel is deleted from the frequency hopping frame.

16. The method of claim 13 further comprising programming the implantable and external devices such that when a particular communications channel is removed from the synchronous channel scan list, the time slot assigned to the removed communications channel is assigned to another previously unused communications channel or, if no previously unused communications channel is available, the time slot assigned to the removed communications channel is deleted from the frequency hopping frame.

17. The method of claim 13 further comprising programming the external device to modify the synchronous channel scan list to remove one or more particular communications channels from the synchronous channel scan list upon detection of a degradation in the quality of those particular communications channels and to transmit the modified synchronous channel scan list to the implantable device.

18. The method of claim 12 wherein the synchronous channel scan list is a subset of a master channel scan list whose entries may be enabled or disabled to form the synchronous channel scan list.

19. The method of claim 18 further comprising programming the implantable and external devices such that the external device may modify the synchronous channel scan list to remove a particular communications channel from the synchronous channel scan list upon detection of a degradation in the quality of that communications channel by transmitting a command to the implantable device that disables the entry for that communications channel in the master channel scan list and to add a particular communications channel to the synchronous channel scan list by transmitting a command to the implantable device that enables the entry for that communications channel in the master channel scan list.

20. The method of claim 18 further comprising programming the implantable and external devices such that the external device may modify the synchronous channel scan list by transmitting to the implantable device a channel scan mask that enables or disables entries of the master channel scan list.

* * * * *